United States Patent [19]

Leston

[11] 4,431,846
[45] Feb. 14, 1984

[54] REDUCTION OF O-ETHYLPHENOL IN M,P-CRESOL BY PREFERENTIAL T-BUTYLATION

[75] Inventor: Gerd Leston, Pittsburgh, Pa.

[73] Assignee: Koppers Company, Inc., Pittsburgh, Pa.

[21] Appl. No.: 381,159

[22] Filed: May 24, 1982

[51] Int. Cl.$^3$ .............................................. C07C 37/68
[52] U.S. Cl. ..................................... 568/750; 568/751; 568/783
[58] Field of Search ............... 568/750, 751, 752, 756, 568/784, 805, 783

[56] References Cited

U.S. PATENT DOCUMENTS

| | | | |
|---|---|---|---|
| 2,297,588 | 9/1942 | Stevens et al. | 568/756 |
| 2,435,087 | 1/1948 | Luten | 568/750 |
| 2,497,972 | 2/1950 | Basterfield | 568/756 |
| 3,534,111 | 10/1970 | Hess | 568/788 |
| 4,149,026 | 2/1981 | Dodd | 568/788 |

FOREIGN PATENT DOCUMENTS

| | | | |
|---|---|---|---|
| 1145629 | 3/1963 | Fed. Rep. of Germany | 568/756 |
| 2215451 | 11/1972 | Fed. Rep. of Germany | 568/756 |
| 557519 | 11/1943 | United Kingdom | 568/756 |

OTHER PUBLICATIONS

Stevens, "Industrial and Engineering Chemistry", vol. 35, No. 6, (1943), pp. 655–660.

*Primary Examiner*—Werren B. Lone
*Attorney, Agent, or Firm*—Daniel J. Long; Herbert J. Zeh, Jr.

[57] ABSTRACT

A process is disclosed for reducing the concentration of o-ethylphenol in m,p-cresol by partially t-butylating a mixture of the above and equilibrating the resultant mixture to convert o-ethylphenol and its 6-t-butyl derivative to the thermodynamically most stable 4-t-butyl-o-ethylphenol. The resultant mixture may then be separated by fractional distillation to isolate m,p-cresol low in o-ethylphenol, optionally, the mono-t-butylated derivatives of m,p-cresol and leave behind the 4-t-butyl-o-ethylphenol, along with di-t-butylated derivatives of all the phenols.

13 Claims, 1 Drawing Figure

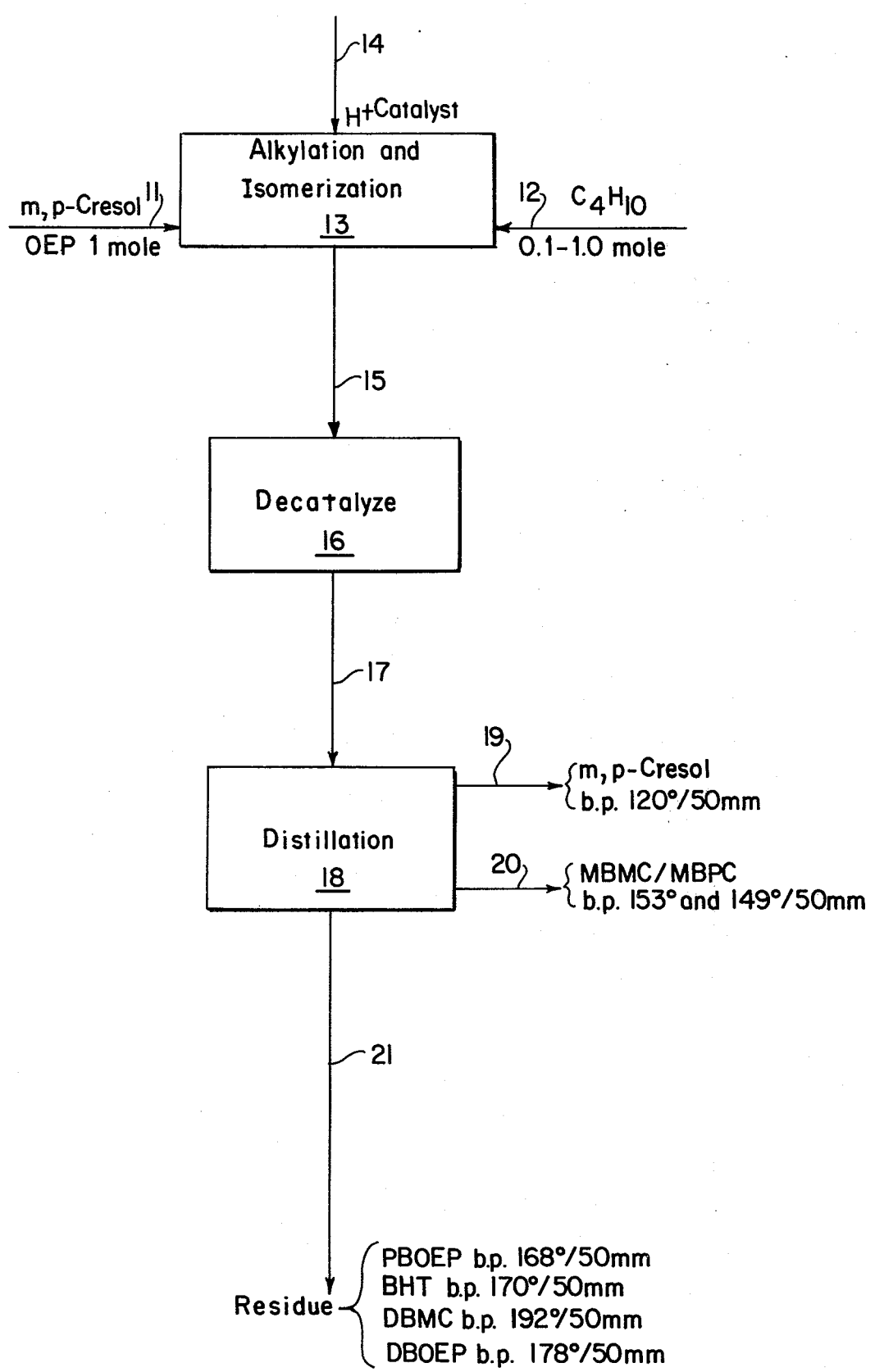

REDUCTION OF O-ETHYLPHENOL IN M,P-CRESOL BY PREFERENTIAL T-BUTYLATION

BACKGROUND OF THE INVENTION

1. Field of the Invention

This invention relates generally to meta, para-cresol mixtures and more particularly to a process for the reduction of the content of the impurity ortho-ethylphenol from a mixture of meta-, para-cresol isomers.

2. Description of the Prior Art

The cresols, $CH_3C_6H_4OH$, exist in three isomeric forms. The ortho-isomer has a boiling point such that it can be readily separated from the m- and p- isomers by distillation. However, the meta- and para- isomers have boiling points which are too close together for the two isomers to be separated by fractional distillation. Consequently, ortho-cresol is marketed as the isomer, itself, but m- and p-cresols are marketed generally as a mixture under a specification of 2°, 3° or 5° C. including the true boiling points of m- and p-cresol.

The major source of commercial cresols is from the tar produced by the coking of coal. Another source is from cracked petroleum distillates. However, the mixture of m- and p-cresols that is derived from petroleum sources tends to be contaminated with o-ethylphenol.

In the two major outlets that use a mixture of the cresols, m,p-cresol, as a starting material, the impurity o-ethylphenol is undesirable. When the cresol mixture is used in the manufacture of tricresyl phosphates, which are used as plasticizers and heat transfer media, any resultant phosphates made in part or in toto from ortho-alkylphenols such as o-cresol and o-ethylphenol are poisonous to mammals. The other major use for m,p-cresol is as starting material for the manufacture of butylated derivatives which are antioxidants such as butylated hydroxytoluene (BHT) or intermediates for antioxidants, and impurities here should be minimized. As is shown in the table of boiling points of these derivatives below, even the t-butylated o-ethylphenols boil at temperatures so close to those of the butylated derivatives of m,p-cresols that the isolation of these compounds is difficult.

Typical of commercially available mixtures of m- and p-cresols from a petroleum source is a material which is sold as M-P 88, a tar acid blend produced by the Productol Chemical Division of Ferro Corporation, and which contains a minimum of 88% m,p-cresol, about 0.5–6% of o-ethylphenol (OEP) and lesser amounts of o-cresol, 2,4- , 2,5-xylenol and phenol. The difficulty of removing o-ethylphenol from m,p-cresol by fractional dishtillation may be seen by examining the boiling points expressed in degrees centigrade at various pressures expressed in millimeters of mercury absolute:

| Compound | Boiling Point | | |
|---|---|---|---|
| | 50 mm | 100 mm | 760 mm |
| m,p-cresol | 120 | 137 | 202 |
| 2-ethylphenol | 121 | 139 | 204 |

The patent and chemical literature describe numerous processes for separating the pure meta and para isomers from the meta-para mixture. A preferred process is an alkylation procedure. According to this process the mixture is alkylated with isobutylene, the di-tert-butylated products are separated by fractional distillation, and the butylated products are debutylated. The products recovered are m-cresol, p-cresol and isobutylene.

The foregoing process is not feasible for the separation of the o-ethylene derivative from the other. The following table showing the boiling points of the t-butylated derivatives of m,p-cresols and o-ethylphenol at various pressures demonstrates why it is so difficult to separate the ortho-ethylphenol by means of a process that is designed to produce pure di-t-butylated cresol isomers.

| Compound | Boiling Point °C. Pressures in mm Hg | | |
|---|---|---|---|
| | 50 mm | 100 mm | 760 mm |
| 2-t-butyl-p-cresol (MBPC) | 149 | 168 | 238 |
| 6-t-butyl-m-cresol (MBMC) | 153 | 172 | 243 |
| 6-t-butyl-2-ethylphenol (OBOEP) | 152 | | |
| 4-t-butyl-2-ethylphenol (PBOEP) | 168 | 187 | 254 |
| 2-6-di-t-butyl-p-cresol (BHT) | 170 | 190 | 266 |
| 4-6-di-t-butyl-2-ethylphenol (DBOEP) | 178 | | |
| 4,6-di-t-butyl-m-cresol (DBMC) | 192 | 211 | 282 |

SUMMARY OF THE INVENTION

I have now found that a major portion of the impurity, ortho-ethylphenol, that is found in the mixture m-p-cresol which is obtained from petroleum sources can be removed by the preferential t-butylation of this impurity under equilibrating conditions. By equilibrating conditions, I mean reaction conditions of catalyst strength, catalyst concentration, concentration of reactants, time, and temperature to approach equilibrium of the components of the reaction mixture in accordance with the thermodynamic stabilities of the said components under the said reaction conditions.

I have found the 4-t-butyl-o-ethylphenol to be thermodynamically the most stable t-butylated derivative when compared with the hindered p-t-butylated phenols such as 4-6-di-t-butyl-m-cresol, 4-t-butyl-m-cresol and 4-t-butyl-2,5-xylenol.

The T-butylation of a mixture of m,p-cresol containing o-ethylphenol either under conditions leading to equilibration or followed by such conditions will convert a disproportionately large amount of OEP to its 4-t-butyl derivative from which the desirable products can then be separated by distillation.

The objects, features, and advantages of the invention will become more apparent during the course of the following description when taken in conjunction with the accompanying drawing.

BRIEF DESCRIPTION OF THE DRAWING

The single sheet of drawing is a generally schematic illustration of the preferred embodiment of the process of this invention.

DETAILED DESCRIPTION OF THE INVENTION

Procedures for the formation of butylated phenols are well known. Referring to the drawing, (a) the mixture of m,p-cresol may by way of line 11 and (b) the alkylating agent, such as isobutylene, may by way of line 12 be fed to the alkylation and isomerization zone 13 where (c) the catalyst is shown as being introduced by way of line 14. After the alkylation reaction, the reaction mass may be fed by way of line 15 to a decatalization zone 16 where the catalyst, depending upon its type, is neutralized or removed by filtration. The reaction mass may then be fed by way of line 17 to a distillation zone 18 where the lower boiling fraction, m,p-cresol, may be removed by way of line 19, the higher boiling fraction, the monobutylated cresols, may be removed by way of line 20, and the residue, the unwanted o-ethylphenol derivative, may be removed by way of line 21.

I have found that in carrying out my invention, the particular acidic catalyst to be used is not critical so long as it is sufficiently strong to effect equilibration. Sulfuric acid, m-benzenedisulfonic acid, and a macroreticular sulfonated ion-exchange resin that is sold by Rohm and Haas under the trademark AMERLYST 15 have been used.

Several sources of t-butyl groups such as isobutylene, t-butyl alcohol, t-butyl chloride, diisobutylene, t-butylated meta- and/or paracresols such, for example, as 2-t-butyl-p-cresol, 2,6-di-t-butyl-p-cresol, 6-t-butyl-m-cresol and 4,6-di-t-butyl-m-cresol, may be used. If a butylated cresol is used as source for t-butyl groups, the term transbutylation is usually applied. If diisobutylene is used, depolymerization-butylation is said to take place. The butylation or transbutylation may take place from 0° C. to 150° C., preferably at 50°–150° C. to achieve desirable reaction rates.

The equilibrating temperature is preferably in the range of 100°–160° C. Below this temperature, the rate of equilibration is slow and above this range undesirable de-t-butylation of 4-butyl-ortho-ethylphenol takes place as shown below by Sample 5 in Example III and Table VI. The reactions, both the t-butylation and the equilibration, are usually performed at atmospheric pressure although subatmospheric pressures, for example, 50 mm mercury, at which the phenols such as m,p-cresol and OEP do not distill, and superatmospheric pressures, for example, 10 atmospheres, may be used.

The molar proportion of t-butyl groups to the phenol mixture is not critical, and can be in the range of 1:1 based on OEP contained to 1:1 or higher based on total phenols. The preferred molar ratio of t-butyl groups to total phenols is preferably in the range of 0.1:1.0 to about 1.0:1.0 assuming an OEP content of 5-10%. Ratios below 0.2:1.0 leave too much OEP in the equilibrated mixture to be desirable. Ratios above about 1.0:1.0 produce too much di-t-butylated m,p-cresols which will codistill with 4-t-butyl-ortho-ethylphenol and 4,6-di-t-butyl-o-ethylphenol and will thus represent a loss of desirable products.

The particular source or composition of the m,p-cresol mixture which contains the impurity o-ethylphenol and from which it is desired to reduce the content is not critical. In the examples described below an m,p-cresol mixture (M-P 88) was used which had the following analysis by weight percentage.

o-cresol: trace
m,p-cresol: 87.5
o-ethyl phenol: 6.9
2,6,-xylenol: 1.8
2,4-2,5-xylenol: 3.2
unknown: 0.4

The following examples illustrate further the practice of the invention.

EXAMPLE I

A mixture of 216 g (2.0 moles) of a mixture (M-P 88) of meta-, para-cresols containing as an undesirable compound o-ethylphenol and 1.0 g m-benzenesulfonic acid was stirred in a flask while 78.4 g (1.4 moles) of isobutylene was sparged under the surface at 25°–100° C. At the completion of the isobutylene addition, Sample No. 1 was withdrawn for gas chromatography analysis. Thereafter, the mixture was heated at 150° C. for seven hours with stirring, and then Sample No. 2 was withdrawn for gas chromotography analysis. Then the reaction mixture was cooled to room temperature and filtered to remove any insoluble catalyst. Next, 1.0 g of crushed NaOH was added to deactivate the catalyst and the mixture was stirred at 50° C. for 40 minutes and Sample No. 3 was withdrawn. Gas chromotography analysis of the three samples are shown in Table I.

TABLE I

|  | Sample No. | | |
|---|---|---|---|
|  | 1 | 2 | 3 |
| m,p-cresol | 15.8 | 32.5 | 45.3 |
| 2,6-xylenol | 0.9 | | |
| OEP | 1.3 | >0.1 | >0.1 |
| 2,4-2,5-xylenol | 1.3 | 1.0 | 2.0 |
| MBPC | 20.1 | 17.7 | 14.7 |
| MBMC | 52.3 | 35.0 | 26.3 |
| PBOEP | 2.1 | 5.5 | 5.8 |
| BHT | 2.6 | 1.1 | 0.7 |
| DBOEP | 2.0 | 1.6 | 1.0 |
| DBMC | 1.3 | 2.4 | 1.2 |

The product about 278 g. was distilled through a 2-foot stainless steel Canon-packed column at a pressure of 50 mm mercury with details shown in Table II.

TABLE II

| Boiling Point, °C. | Reflux Ratio | Cut No. | Amount, q. |
|---|---|---|---|
| 101 | 99/1 | 1 | 27.6 |
| 90 | 99/1 | 2 | 18.7 |
| 116 | 10/1 | 3 | 43.5 |
| 120 | 10/1 to 39/1 | 4 | 24.6 |
| 142 | 99/1 | 5 | 41.9 |
| 150 | 99/1 | 6 | 32.3 |
| 158 | 99/1 | 7 | 27.8 |
| 171 | 99/1 | 8 | 16.8 |
| Residue |  | 9 | 44 |

These cuts were then analyzed by gas chromatography with the results being shown in Table III.

TABLE III

| Chemical | Distillation Cuts | | | | | | | | |
|---|---|---|---|---|---|---|---|---|---|
|  | 1 | 2 | 3 | 4 | 5 | 6 | 7 | 8 | 9 |
| m,p-cresol | 97.1 | 98.0 | 98.7 | 84.8 | 1.3 | 0.2 | 0.6 | 2.1 | 0.4 |
| 2,6-xylenol |  |  |  |  |  |  |  |  |  |
| OEP | 0.5 | 0.5 | 0.5 | 0.3 |  |  |  |  |  |
| 2,4-2,5-xylenol | 0.7 | 1.2 | 0.8 | 11.2 | 0.4 |  |  |  | 0.3 |
| MBPC | 0.3 | 0.2 |  | 2.7 | 55.4 | 29.1 | 3.3 | 0.5 |  |
| MBMC | 0.6 |  |  | 0.9 | 42.0 | 69.3 | 71.7 | 0.5 |  |
| PBOEP |  |  |  |  |  | 0.2 | 20.0 | 63.4 | 0.5 |
| DBPC |  |  |  |  |  |  |  | 1.9 |  |
| DBOEP |  |  |  |  |  |  |  | 4.3 | 3.0 |

TABLE III-continued

| Chemical | Distillation Cuts | | | | | | | | |
|---|---|---|---|---|---|---|---|---|---|
| | 1 | 2 | 3 | 4 | 5 | 6 | 7 | 8 | 9 |
| DBMC | | | | | | | | | 27.7 |

*All values in area percent.

The results, presented in Table I show that the ortho-ethylphenol level was reduced from 1.3% after alkylation to less than 0.1% after equilibration-partial debutylation at 150° C. Referring to Tables II and III, distillation of this mixture shows 0.5% max. OEP in the cresol cuts 1, 2, and 3, with PBOEP low (0.2%) in Cut 6, rising to 20% in Cut 7 and finally concentrating to 63% in Cut 8 as the boiling point rises.

EXAMPLE II

A mixture of 540.0 g (ca. 5.0 moles) of the m-, p-cresol mixture (M-P 88) and 2.0 g m-benzenedisulfonic acid was sparged with isobutylene (not measured) at 25°–100° C. during a period of four hours. The weight gain was 196.8 g (3.5 moles). Sample 1 was taken at this time. The mixture was next stirred at 151°–153° C. for seven hours and, on cooling, 1.9 g of catalyst was filtered. To the rest, 0.2 g of crushed NaOH was added to insure neutralization of the acid and 2 g of Sample 2 was removed.

Samples were analyzed by gas chromatography with the results shown in Table IV.

TABLE IV

| Chemical | Sample 1 | Sample 2 | Residue |
|---|---|---|---|
| $(C_4)_x$ [2] | 0.7 | 3.9 | |
| o-cresol | 0.5 | | |
| o-ethylphenol | 5.1 | 0.7 | |
| m,p-cresol | 25.4 | 34.7 | |
| MBMC/MBPC | 63.2 | | Small |
| 4-t-butyl-ortho-ethylphenol | | 55.7 | Major |
| other (unknown) | | 2.0 | Major |
| DBMC | | 2.9 | Major |

[1] All analyses in area percent
[2] Isobutylene oligomer

The material was next distilled in a 2-foot Canon-packed column at 50 mm mercury with the results shown in Table V.

TABLE V

| Head Temp. °C. | Reflux Ratio | Fraction No. | Amount ml. | g |
|---|---|---|---|---|
| 90 | 19 | 1 | 23 | 17.68 |
| 116 | 19 | 2 | 11 | 11.57 |
| 116 | 19 | 3 | 11 | 12.04 |
| 116 | 9 | 4 | 19 | 19.17 |
| 119 | 9 | 5 | 48 | 48.13 |
| 119 | 9 | 6 | 47 | 48.24 |
| 119 | 9 | 7 | 50 | 50.82 |
| 118 | 9 | 8 | 5± | 51.98 |
| 118 | 9 | 9 | 51 | 52.07 |
| 120 | 9 | 10 | 50 | 51.30 |
| 120 | 9 | 11 | 50 | 51.25 |
| 120 | 9 | 12 | 52 | 53.2 |
| 121 | 19 | 13 | 37 | 37.83 |
| 125 | 19 | 14 | 5.0 | 5.6 |
| 146 | 19 | 15 | 12.0 | 11.60 |
| Flashed over at 20 mm | | 16 | 13.6 | 12.85 |
| Hold-up | | | | 7.43 |
| Residue | | | | 16.2 |

The dry ice traps contained considerable quantities of isobutylene.

The analyses of the samples and the isolation of a large quantity of isobutylene in the dry ice trap point to dealkylation of the major products MBMC/MBPC but not of 4-t-butyl-o-ethylphenol.

As can be seen, the ortho-ethylphenol (OEP) was converted almost exclusively to its 4-t-butyl derivative (PBOEP). The gas chromatographic analysis found no OEP. The difference between this Example II and the prior Example I is that the butylation described in Example II was carried out longer than in the prior Example I. This means that a higher degree of butylation will convert essentially all OEP to PBOEP. These conditions would also produce quantities of MBMC and MBPC but these could readily be separated from PBOEP by distillation and recycle distillation.

EXAMPLE III

A mixture was prepared of 24.4 g (0.20 moles) of o-ethylphenol (98.6%) and 0.20 g of meta-benzenedisulfonic acid was alkylated with 16.8 g (0.30 mole) of isobutylene at 25°–73° C. and Sample 1 was isolated. After raising the temperature to 150° C. during 1.3 hours, Sample 2 was removed. Sample 3 was taken after 0.4 hour at 150° C. and Sample 4 after 1.0 hour at this temperature. Then the temperature was raised to 200° C. during 1.1 hours, at the end of which time Sample 5 was removed. This temperature was maintained for 0.5 hour, the stirred mixture was cooled to 50° C. and Sample 6 was taken.

The samples were analyzed by gas chromatography with the results shown in Table VI.

TABLE VI

| Component | Retention Time (min.) | Sample | | | | | |
|---|---|---|---|---|---|---|---|
| | | 1 | 2 | 3 | 4 | 5 | 6 |
| OEP | 2.8 | 3.8 | 3.1 | 0.9 | 1.2 | 14.5 | 17.4 |
| 6-t-Butyl-OEP | 8.0 | 33.9 | 25.9 | 0.9 | 0.9 | 1.2 | 1.1 |
| 4-t-Butyl-OEP | 10.2 | 3.7 | 16.6 | 61.3 | 65.1 | 68.6 | 63.3 |
| 4,6-Di-t-Butyl-OEP | 21.0 | 57.2 | 53.8 | 31.8 | 27.1 | 4.8 | 3.4 |

*All analyses in area percent

Table VI shows the t-butylation of neat OEP, the initial decrease of OEP on isomerization at 150° C. from 3.8% to 1% with concurrent decrease of 6-t-butyl-OEP from 34% to 0.9%. At the same time, the concentration of the thermodynamically more stable PBOEP rises from 4% to 65%. Further heating at 200° C. in the presence of acid catalyst causes debutylation as seen by increasing OEP concentration to 17% and decreasing dibutyl-OEP concentration, while having little effect on the PBOEP concentration.

EXAMPLE IV

A 100 g sample of the m-, p-cresol mixture (M-P 88) and 0.50 g (0.5% based on the weight of cresol mixture) of conc. $H_2SO_4$ were introduced into a 250 ml Morton flask, stirred and warmed to 40°–50° C. while 10 g of isobutylene was bubbled into the liquid. Not all of the isobutylene had been absorbed by the tar acid as seen by a bubbler on the exit side of the system. Sample 1 was taken at the end of the addition. The sample by gas chromatography analyzed the same as M-P 88 but with small peak after m-cresol, tentatively identified as MBPC and larger peak (MBMC tentatively).

Then the temperature was raised to 175° C. Sample 2 was taken after one hour. This Sample 2 showed more MBPC and less MBMC than Sample 1, as well as a later peak (PBOEP); OEP was decreasing. Then Sample 3 was taken after two hours, and Sample 4 was taken after four hours. Sample 3 showed still more PBOEP, less o-cresol and less OEP, and Sample 4 was similar to Sample 3. The heating and stirring were continued over the weekend and Sample 5 was taken. The fifth sample showed the OEP to be 1.3%.

The following Examples V and VI show transbutylation, i.e., shifting of the t-butyl group from MBMC (Example V) or DBMC (Example VI) to OEP.

EXAMPLE V

To 100 g of the m-, p-cresol mixture (M-P 88) was added 0.25 g m-benzenedisulfonic acid and 15.0 g MBMC and Sample 1 was taken. The overall molar ratio of t-butyl groups to total phenols was 0.09:1.0 as calculated from 88 g of cresols, 12 g of mixed xylenols and ethylphenols and 15 g of MBMC. Sample 2 was taken the following morning, and then the mixture was stirred and heated at 170°–175° C. with Samples 3, 4 and 5 being taken after one, two and four hours, respectively. Semiquantitative gas chromatographic analysis showed Samples 1 and 2 to be the ingredient M-P 88 with added MBMC; no significant reaction had occured. In Sample 3, the OEP has been reduced by about one-half, MBMC was also reduced, and some MBPC and PBOEP had appeared. Sample 4 looked similar to Sample 3 except the OEP amount seemed to be smaller. Sample 5 showed roughly similar amounts of MBMC and PBOEP and a smaller amount of MBPC. A quantitative gas chromatographic analysis found this last sample to contain 1.7% OEP.

EXAMPLE VI

A mixture of 100 g of the m-, p-cresol mixture (M-P 88), 1.00 g of dry ion exchange resin sold under the trademark Amberlyst 15 and 10.00 g DBMC was prepared and sampled. The overall molar ratio of t-butyl groups to total phenols was 0.094:1.0. The mixture was stirred and maintained at a temperature of 150°–5° C. Samples were taken after one, two and four hours. The later samples showed less color than the original material. Semiquantitative gas chromatographic analyses showed DBMC in Sample 1 but very little, if any, in Sample 2. Instead, there was MBMC and lesser amounts of MBPC and PBOEP. Samples 3 and 4 showed much reduced OEP and equal amounts of MBMC and PBOEP along with a lesser amount of MBPC. The quantitative gas chromatographic analysis found 1.6% OEP in this fourth sample.

The foregoing has presented a process for removing the amount of the impurity o-ethylphenol from a mixture of m-, p-cresol isomers. The impurity is particularly found in such cresol mixtures as are obtained from petroleum sources.

What is claimed is:

1. A process for reducing the amount of ortho-ethylphenol impurity contained in a mixture of meta and para isomers of cresol comprising the steps of:
   (a) alkylating at a temperature of from about 0° C. to about 150° C. with a t-butyl group obtained from a compound selected from the group consisting of isobutylene, t-butylalcohol, t-butyl chloride, diisobutylene, t-butylated meta-cresols and t-butylated para-cresols to give a final molar ratio of t-butyl groups to total ortho-ethylphenol and meta and para-cresols of about 0.1:1.0 to about 1.0:1.0 in the presence of an acidic catalyst of sufficient acid strength to catalyze said alkylation;
   (b) equilibrating the t-butylated mixture at a temperature from about 100° C. to about 160° C. to reduce the content of ortho-ethylphenol and raise the level of 4-t-butyl-o-ethylphenol in the presence of said catalyst;
   (c) removing said catalyst; and
   (d) fractionally distilling the mixture to obtain the meta-, para-cresol mixture with a reduced content of ortho-ethylphenol impurity, and leaving the p-t-butyl-o-ethylphenol derivative of said impurity as residue.

2. The process of claim 1 wherein both the meta and para isomers and their mono-ortho-t-butylated derivatives are separated from p-t-butyl-o-ethylphenol.

3. The process of claim 1 wherein the source of t-butyl groups is isobutylene, t-butyl alcohol, t-butyl chloride, 2-t-butyl-p-cresol, 2,6-di-t-butyl-p-cresol, 6-t-butyl-m-cresol, or 4,6-di-t-butyl-m-cresol.

4. The process of claim 1 wherein the acid catalyst is sulfuric acid.

5. The process of claim 1 wherein the acid catalyst is m-benzenedisulfonic acid.

6. The process of claim 1 wherein the acid catalyst is a sulfonic acid ion-exchange resin.

7. The process of claim 1 wherein the concentration of catalyst to total phenols is in the range from about 0.1% to about 20%.

8. The process of claim 1 wherein the alkylation temperature is in the range from about 25° C. to about 160° C.

9. The process of claim 1 wherein the equilibration temperature is in the range from about 100° C. to about 160° C.

10. The process of claim 1 wherein the pressure is from about 50 mm Kg absolute to about 10 atm.

11. The process of claim 1 wherein the acid catalyst is neutralized with aqueous sodium hydroxide.

12. The process of claim 6 wherein the sulfonic acid ion-exchange catalyst is removed by filtration, or centrifugation or said catalyst is mechanically trapped in a fixed bed reactor.

13. The process of claim 1 wherein step (c) is carried out by deactivating the catalyst.

* * * * *